United States Patent
Kita et al.

(10) Patent No.: US 7,282,589 B2
(45) Date of Patent: Oct. 16, 2007

(54) ACID ADDITION SALT OF OPTICALLY ACTIVE PIPERIDINE COMPOUND AND PROCESS FOR PREPARING THE SAME

(75) Inventors: Jun-ichiro Kita, Ube (JP); Shinji Takamura, Ube (JP)

(73) Assignees: UBE Industries, Ltd., Ube-shi (JP); Tanabe Seiyaku Co., Ltd., Osaka-shi (JP)

( * ) Notice: Subject to any disclaimer, the term of this patent is extended or adjusted under 35 U.S.C. 154(b) by 461 days.

(21) Appl. No.: 10/771,361

(22) Filed: Feb. 5, 2004

(65) Prior Publication Data

US 2004/0220226 A1 Nov. 4, 2004

Related U.S. Application Data

(62) Division of application No. 09/949,809, filed on Sep. 12, 2001, now Pat. No. 6,780,877, which is a division of application No. 09/331,792, filed as application No. PCT/JP97/04826 on Dec. 25, 1997, now Pat. No. 6,307,052.

(30) Foreign Application Priority Data

| Dec. 26, 1996 | (JP) | ................................... 8-347851 |
| Dec. 26, 1996 | (JP) | ................................... 8-347853 |
| Dec. 26, 1996 | (JP) | ................................... 8-347895 |

(51) Int. Cl.
*C07D 401/12* (2006.01)
(52) U.S. Cl. .................................................... 546/194
(58) Field of Classification Search ................ 546/194
See application file for complete search history.

(56) References Cited

U.S. PATENT DOCUMENTS

| 4,929,618 A | 5/1990 | Koda et al. .................. 514/253 |
| 5,081,277 A | 1/1992 | Rossey et al. ................. 560/17 |
| 5,225,559 A | 7/1993 | Kita et al. .................... 546/194 |
| 5,281,592 A | 1/1994 | Ozeki et al. ............. 514/224.2 |

FOREIGN PATENT DOCUMENTS

| JP | 225465 A | 7/1988 |
| JP | 64-013090 | * 1/1989 |
| JP | 1-242574 A | 9/1989 |
| JP | 4-182467 A | 6/1992 |
| JP | 5-345759 A | 12/1993 |
| JP | 6-135958 A | 5/1994 |
| JP | 6-239742 A | 8/1994 |
| JP | 6-336480 A | 12/1994 |
| JP | 6-413090 | 1/1998 |
| JP | 10-182635 | 7/1998 |
| JP | 10-237069 | * 8/1998 |

OTHER PUBLICATIONS

March "Advanced organic chemistry . . . " McGraw-hill, pp. 71-72 (1968).*
Shoei et al. "Preparation of Xanthine . . . " CA 111:133914 (1989).*
Kita et al. "Preparation of diarylmethoxypiperidine . . . " CA 117:131083 (1992).*
Yoshida et al. "Racemization of . . . " CA 129:245051 (1998).*
Inue et al. "Synthesis of halogen-substituted . . . " J. Med. Chem. 34 p. 675-687 (1991).*
Japan Chemical Society, "Experimental Chemistry", vol. 18, pp. 504-505 (1957).
Yoshida et al., "Method for Purification of 4-pyridylphenylmethoxypiperdine derivatives", CA 122:187405, (1994).

* cited by examiner

*Primary Examiner*—Celia Chang
(74) *Attorney, Agent, or Firm*—Birch, Stewart, Kolasch & Birch, LLP

(57) ABSTRACT

(S)-(−)-4-[(4-chlorophenyl)(2-pyridyl)methoxy]piperi-dine represented by the formula (IV):

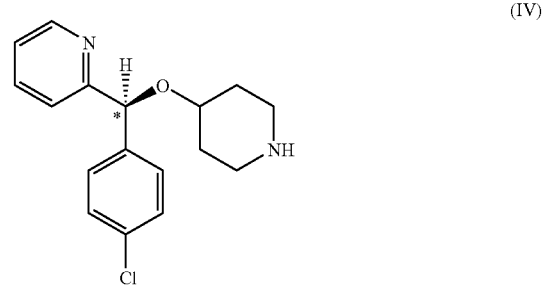

(IV)

wherein * represents an asymmetric carbon.

1 Claim, No Drawings

ACID ADDITION SALT OF OPTICALLY ACTIVE PIPERIDINE COMPOUND AND PROCESS FOR PREPARING THE SAME

This application is a Rule 53(b) Divisional of Application No. 09/949,809, filed on Sep. 12, 2001 now U.S. Pat. No. 6,708,877, which is a Rule 53(b) Divisional of Application No. 09/331,792 filed on Jun. 25, 1999, now U.S. Pat. No. 6,307,052 for which priority is claimed under 35 U.S.C. § 120; and this application claims priority of International Application PCT/JP97/04826 filed on Dec. 25, 1997, under the Patent Cooperation Treaty and Application No. 347851/1996 filed in Japan on Dec. 26, 1996, Application No. 347853/1996 filed in Japan on Dec. 26, 1996, and Application No. 347895/1996 filed in Japan on Dec. 26, 1996, under 35 U.S.C. 119. The entire contents of which are hereby incorporated by reference.

TECHNICAL FIELD

This invention relates to benzenesulfonic acid salt or benzoic acid salt of (S)-4-[4-[(4-chlorophenyl)(2-pyridyl)methoxy]piperidino]butanoic acid which is excellent in antihistaminic activity and antiallergic activity, a process for preparing the same, and an optically resolving method of 4-[(4-chlorophenyl)(2-pyridyl)methoxy]piperidine which is important as a racemic intermediate thereof. The acid addition salt has little hygroscopicity and excellent in physicochemical stability so that it is particularly suitable compound as a medicine. Also, the present invention relates to a medical composition containing the compound as an effective ingredient.

BACKGROUND ART

A piperidine compound (II) represented by the formula (II):

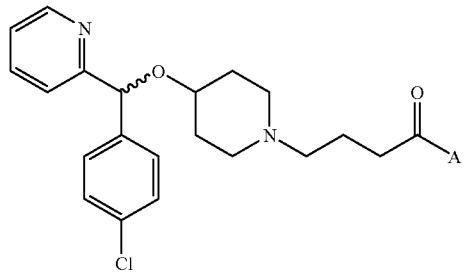

(II)

wherein A represents a lower alkyl group, hydroxyl group, a lower alkoxy group, amino group, a lower alkylamino group, phenyl group or a lower alkyl-substituted phenyl group, or a salt thereof described in Japanese Provisional Patent Publication No. 25465/1990 has characteristics that a secondary effect such as stimulation or suppression on the central nerves, which often appears in the conventional antihistaminic compound, can be reduced as little as possible, and is expected to be a medicine for therapeutic treatment of allergic skin diseases such as a nettle rash, eczema, dermatitis and the like, allergic rhinitis, sneeze, mucus, cough due to respiratory inflammation such as cold and the like, and bronchial asthma.

For producing the piperidine compound (II) effectively as a more preferred optical isomer for a medicine, it is desired to use the optically resolved product as a starting material by optically resolving an intermediate. However, this piperidine compound (II) has one asymmetric carbon atom but the method of isolating its optically active isomer from the racemic mixture has not been known as of today.

It has been generally known that optical isomers show different pharmacological activity or safety and there are also differences in the metabolic rates and the protein binding ratios therebetween (Pharmacia, 25 (4), pp. 311-336, 1989). Accordingly, for providing a medicine, a pharmaceutically preferable optical isomer with high optical purity is required. Also, in order to secure high quality of said optical isomer as a medicine, it is desirable that the isomer has superior properties in physicochemical stability.

The present inventors have studied intensively to solve the above problems. As the result, they have found that a benzenesulfonic acid salt or a benzoic acid salt of optically active (S)-4-[4-[(4-chlorophenyl)(2-pyridyl)methoxy]-piperidino]butanoic acid represented by the following formula (I) has excellent stability which is preferred as a medicine whereby accomplished the present invention.

DISCLOSURE OF THE INVENTION

The first invention relates to a benzenesulfonic acid salt or a benzoic acid salt of an optically active piperidine compound (I) represented by the formula (I):

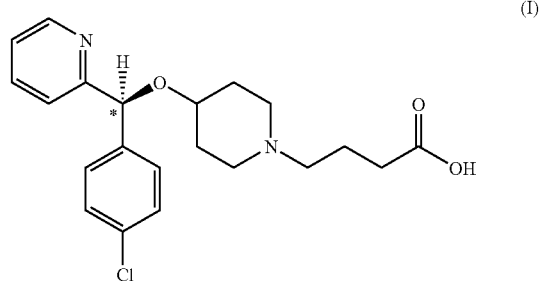

(I)

wherein * represents an asymmetric carbon, which has an absolute configuration of (S).

The second invention relates to a process for preparing a benzenesulfonic acid salt or a benzoic acid salt of an optically active piperidine compound by reacting the optically active piperidine compound represented by the above formula (I) with an absolute configuration of (S) with benzenesulfonic acid or benzoic acid to form a salt.

The third invention relates to a medical composition which comprises a benzenesulfonic acid salt of (S)-4-[4-[(4-chlorophenyl)(2-pyridyl)methoxy]piperidino]butanoic acid or a benzoic acid salt of the same as an effective ingredient.

The invention further relates to a process for preparing a benzenesulfonic acid salt or a benzoic acid salt of the optically active piperidine compound (I) represented by the above formula (I) which comprises reacting (±)-4-[(4-chlorophenyl) (2-pyridyl)methoxy]piperidine with the optically active propionic acid compound (VII) represented by the following formula (VII) or the optically active N-acyl-amino acid; separating and collecting less soluble diastereomeric salt by utilizing the difference in solubilities of the formed two kinds of diastereomeric salts; decomposing the resulting salt; reacting an ester represented by the formula (V):

(V)

wherein R represents a lower alkyl group such as methyl group, ethyl group, etc., and W represents a leaving group such as a halogen atom or a reactive ester group such as methanesulfonyloxy group, p-toluenesulfonyloxy group, etc., with the resulting (S)-4-[(4-chlorophenyl)(2-pyridyl)-methoxy]piperidine to obtain (S)-4-[(4-chlorophenyl)(2-pyridyl) methoxy]piperidine butanoic acid ester represented by the formula (VI):

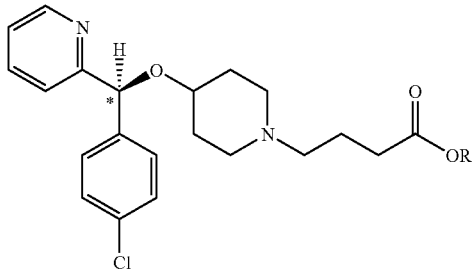

(VI)

wherein R and * have the 'same meaning as defined above, hydrolyzing the resulting compound; and reacting the hydrolyzed compound with benzenesulfonic acid or benzoic acid to form a salt.

BEST MODE FOR CARRYING OUT THE INVENTION

A benzenesulfonic acid salt or a benzoic acid salt of (S)-piperidine compound (I) can be produced by the method represented by the following reaction scheme (1):

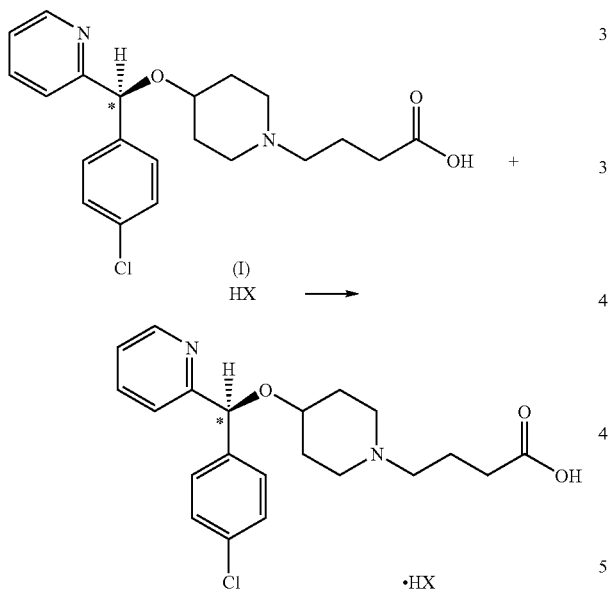

Reaction scheme (1)

wherein HX represents benzenesulfonic acid or benzoic acid, and * has the same meaning as defined above, (hereinafter referred to as a salt-forming reaction).

In the salt-forming reaction, benzenesulfonic acid or benzoic acid can be used in an amount of 0.8 to 2.5-fold mole, preferably 0.9 to 1.2-fold mole based on 1 mole of the (S)-piperidine compound (I).

As a solvent to be used in the salt-forming reaction, it is not particularly limited so long as it does not participate in the reaction, and there may be mentioned, for example, nitrites such as acetonitrile and propionitrile; esters such as methyl acetate and ethyl acetate; alcohols such as methanol, ethanol, 1-propanol, 2-propanol, etc.; acetone, dimethylformamide, etc., and preferably ethanol, 2-propanol, acetonitrile and ethyl acetate. The solvent to be used in the present invention may be used alone or may be in admixture of the above-mentioned two or more kinds of optional solvents.

An amount of the solvent to be used in the salt-forming reaction is usually 0.5 to 30 liters, preferably 0.8 to 20 liters, more preferably 1 to 10 liters per mole of the (S)-piperidine compound (I).

A temperature of the salt-forming reaction is, for example, 5 to 50° C., preferably 10 to 35° C., and a temperature at the time of salt precipitation is, for example, −30° C. to 30° C., preferably −10° C. to 15° C. Also, a method of addition is not particularly limited, but, for example, there may be mentioned a method in which benzenesulfonic acid or benzoic acid dissolved in a solvent is added to a mixed solution of the (S)-piperidine compound (I) and a solvent.

The formed salt of the (S)-piperidine compound (I) can be easily obtained in accordance with the conventional method in this field of technology by, for example, collecting after separation with filtration, centrifugation, etc., washing and then drying.

Next, a process for preparing an (S)-piperidine compound (I) of the present invention will be explained.

The (S)-piperidine compound (I) of the present invention can be prepared by the method shown in the following reaction scheme (2):

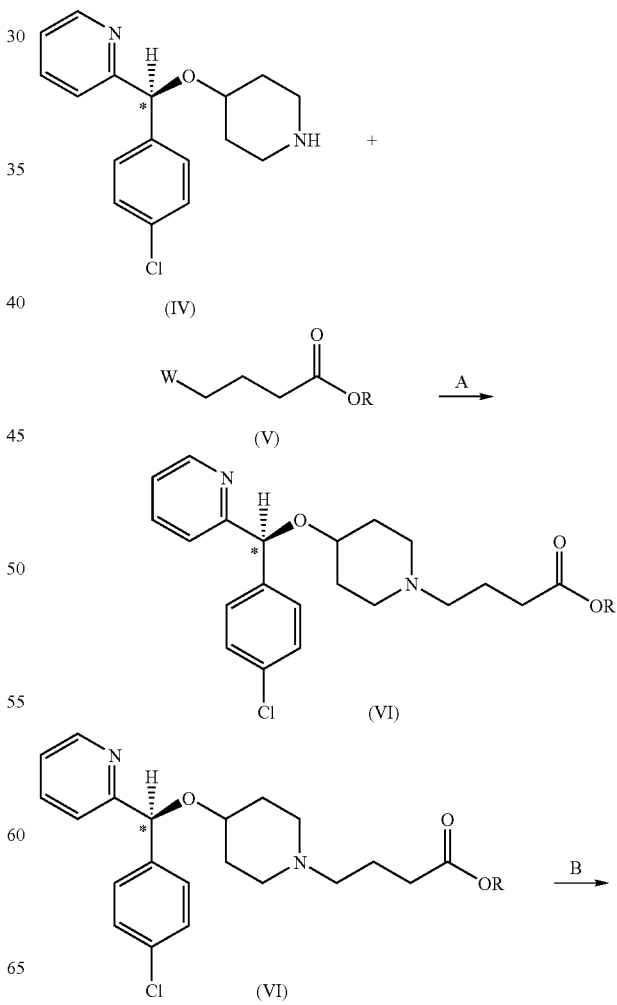

Reaction scheme (2)

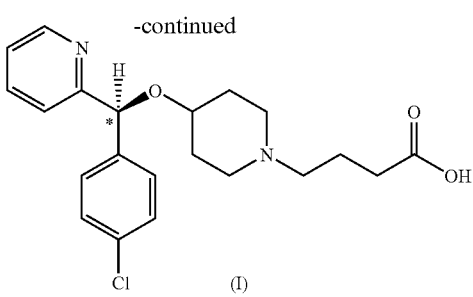

(I)

wherein W represents a leaving group, including a halogen atom such as chlorine atom, bromine atom, iodine atom, etc.; or a reactive ester group such as methanesulfonyloxy group, p-toluenesulfonyloxy group, etc., and R represents a lower alkyl group such as methyl group, ethyl group, etc., and * has the same meaning as defined above.

The step A is an N-alkylation reaction of (S)-piperidine intermediate (IV), and the reaction can proceed by using 1 to 3-fold mole, preferably 1 to 1.5-fold mole of the ester (V) based on 1 mole of the (S)-piperidine intermediate (IV). The above reaction can be carried out in an inert solvent. As a suitable solvent, there may be mentioned, for example, water; lower alcohols such as methanol, ethanol, propanol, butanol, etc.; nitrites such as acetonitrile, propionitrile, etc.; aromatic hydrocarbons such as benzene, toluene, xylene, etc.; ethers such as 1,4-dioxane, tetrahydrofuran, etc.; ketones such as acetone, methyl ethyl ketone, methyl isobutyl ketone, etc.; amides such as N,N-dimethylformamide, etc.; and preferably water, acetonitrile, acetone, and N,N-dimethylformamide. These solvents may be used alone or may be used in admixture of two or more kinds with a suitable mixing ratio.

The reaction is preferably carried out in the presence of a base, and as the preferred base, there may be mentioned, for example, alkali metal hydroxides such as sodium hydroxide, etc.; alkaline earth metal hydroxides such as calcium hydroxide, etc.; alkali metal carbonates such as potassium carbonate, etc.; alkaline earth metal carbonates such as calcium carbonate, etc.; alkali metal hydrogen carbonates such as sodium hydrogen carbonate, etc.; alkali metal hydrides such as sodium hydride, etc.; alkaline earth metal hydrides such as calcium hydride, etc.; alkali metal alkoxides such as sodium methoxide, etc.; trialkylamines such as triethylamine, etc.; and a pyridine compound, etc., and preferably sodium carbonate, potassium carbonate, sodium hydrogen carbonate or potassium hydrogen carbonate. These bases are each used in an amount of 1 to 3-fold moles, preferably 1 to 1.5-fold moles based on 1 mole of the (S)-piperidine intermediate (IV) when the base is monovalent. When the base is divalent, it is used in an amount of 0.5 to 1.5-fold mole, preferably 0.6 to 1-fold mole based on the same.

Also, as a reaction accelerator, a small amount of a metal iodide such as, for example, sodium iodide or potassium iodide may be added. The reaction can be carried out at a reflux temperature of the reaction mixture, for example, 5 to 150° C., preferably 20 to 100° C. The reaction time is 2 to 24 hours.

The step B is a hydrolysis reaction of an (S)-ester (VI). The reaction can be carried out in an aqueous alcohol such as aqueous methanol, aqueous ethanol, etc., and by using an inorganic base such as sodium hydroxide, potassium hydroxide, etc. in an amount of 1 to 5-fold mole, preferably 1 to 3-fold mole per mole of the (S)-ester (VI). A reaction temperature is, for example, 5 to 90° C., preferably 15 to 70° C. A reaction time is generally 1 to 10 hours. After completion of the reaction, the reaction mixture is subjected to neutralization treatment by using a mineral acid such as hydrochloric acid, sulfuric acid, etc. or an organic acid such as acetic acid, oxalic acid, etc. to produce an (S)-piperidine compound (I).

To obtain an optical isomer in general, methods such as an asymmetric synthesis, optical resolution by fractional crystallization or by an enzyme such as lipase, fractionation by an optical resolution column, and the like have been known. For preparing an optically active (S)-piperidine compound (I) efficiently in the present invention, as shown in the following reaction scheme (3):

Reaction scheme (3)

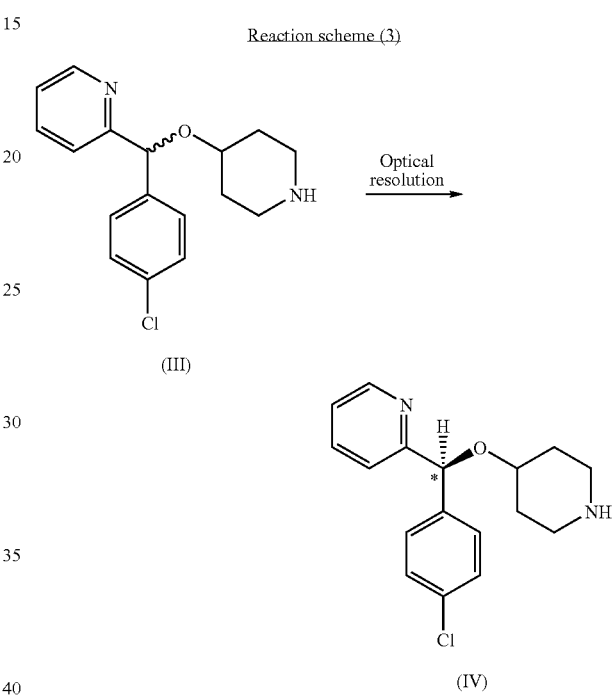

wherein * represents an asymmetric carbon, (±)-4-[(4-chlorophenyl)(2-pyridyl)methoxy]piperidine which is a starting compound and represented by the formula (III) is previously optically resolved and the resulting optically active (S)-4-[(4-chlorophenyl)(2-pyridyl)methoxy]piperidine represented by the formula (IV) is used as a synthetic intermediate.

The said optical resolution can be effectively carried out by the following procedure. That is, by reacting a racemic piperidine compound represented by the formula (III):

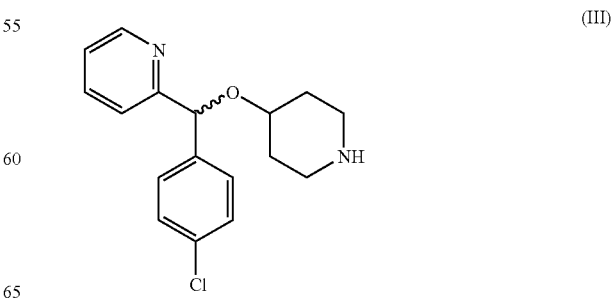

(III)

with an optically active propionic acid compound (VII) represented by the formula (VII):

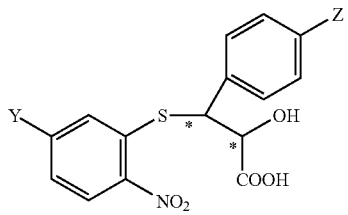

(VII)

wherein Y represents a hydrogen atom or a halogen atom; Z represents a lower alkoxy group; and * represents an asymmetric carbon, or an optically active N-acyl-amino acid, separating and collecting a less soluble diastereomeric salt by utilizing the difference in solubilities of the formed two kinds of diastereomeric salts; and decomposing the resulting salt to give an optically active piperidine intermediate (IV) represented by the formula (IV):

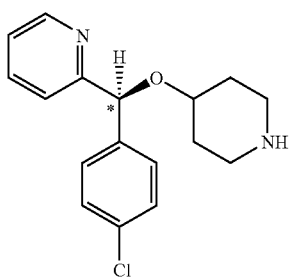

(IV)

wherein * has the same meanings as defined above.

As specific examples of the optically active propionic acid compound (VII) used as an optically resolving agent, there may be mentioned a compound in which, in the formula (VII), Y is hydrogen atom or chlorine atom, and Z is methoxy group. Among these, as preferred examples, there may be mentioned (2R,3R)-2-hydroxy-3-(4-methoxyphenyl)-3-(2-nitro-5-chlorophenylthio)propionic acid and (2R, 3R)-2-hydroxy-3-(4-methoxyphenyl)-3-(2-nitrophenylthio)-propionic acid, and among these, (2R,3R)-2-hydroxy-3-(4-methoxyphenyl)-3-(2-nitro-5-chlorophenylthio)propionic acid is particularly preferred.

Also, as an acyl group of the optically active N-acyl-amino acid which is used as an optically resolving agent, there may be mentioned an aliphatic acyl group such as acetyl group, propionyl group, etc.; an aromatic acyl group such as tosyl group, etc.; and an aralkyloxycarbonyl group such as benzyloxycarbonyl group, etc. The optically active N-acyl-amino acid can be prepared by the well-known acylation of various kinds of neutral, acidic and basic L-amino acids which are constitutional ingredient of protein or non-natural type D-amino acids. As the amino acid, there may be preferably mentioned L-phenylalanine, L-leucine, L-glutamic acid, L-methionine, L-valine, L-threonine and D-phenylglycine.

As the preferred specific examples of the optically active N-acyl-amino acids, there may be mentioned N-acetyl-L-phenylalanine, N-acetyl-L-leucine, N-benzyloxycarbonyl-L-phenylalanine, N-benzyloxycarbonyl-L-valine, N-benzyloxycarbonyl-L-threonine and N-benzyloxycarbonyl-L-serine, and more preferably, there may be mentioned N-acetyl-L-phenylalanine.

An amount of the optically active propionic acid compound (VII) of the formula (VII) or the optically active N-acyl-amino acid to be used as the optically resolving agent is not particularly limited but basically 0.5 to 1.5-fold mole, preferably 0.6 to 1.1-fold mole based on 1 mole of the racemic piperidine intermediate (III) of the formula (III).

As the racemic piperidine intermediate (III) of the formula (III) to be used as the starting material in the present invention, there may be used an equimolar mixture of the (S)-isomer and the (R)-isomer, but the mixing ratio may not necessarily be even and there may be used as a mixture in which either one of the isomers is excessively contained.

The racemic piperidine intermediate (III) of the formula (III) may be used as an acid addition salt such as a hydrochloride. In that case, for example, when a suitable alkali (e.g., sodium hydroxide) is added to the reaction system, a free piperidine compound is produced by causing salt-exchange. Also, the optical isomer of the optically active propionic acid compound (VII) of the formula (VII) or the optically active N-acyl-amino acid may be used as a salt with a base. In that case, when an acid such as hydrochloric acid is added to the reaction system, a free optically active propionic acid compound (VII) or a free optically active N-acyl-amino acid is produced, respectively.

As the solvent to be used for the optical resolution of a racemic piperidine intermediate (III), there may be mentioned, for example, alcohols such as methanol, ethanol, propanol, etc.; ketones such as acetone, methyl ethyl ketone, etc.; esters of a carboxylic acid such as methyl acetate, ethyl acetate, etc.; nitrites such as acetonitrile, propionitrile, etc.; ethers such as dioxane, tetrahydrofuran, etc.; amides such as dimethylformamide, etc.; water and the like. More preferred are esters, nitrites, alcohols or water, and particularly preferred are alcohols or water. These solvents may be used alone but may be used in admixture of two or more kinds with a suitable mixing ratio depending on the necessity, particularly a mixed solvent of alcohols and water is preferred. An amount of the solvent to be used is not particularly limited, but it may be used in an amount of, for example, 2 to 50 parts by weight, preferably 5 to 50 parts by weight based on 1 part by weight of the racemic piperidine intermediate (III).

In the method of optical resolution, the difference in solubilities between the resulting two kinds of diastereomeric salts is sufficiently large so that a less soluble diastereomeric salt can be easily precipitated from a reaction mixture by allowing the mixture to stand or with stirring without any further treatment for crystallization.

With regard to the conditions of dissolving the racemic piperidine intermediate (III) of the formula (III) and the optically active propionic acid compound (VII) of the formula (VII) or the optically active N-acyl-amino acid in a solvent and subsequent precipitation of a less soluble diastereomeric salt, there is no specific limitation. However, dissolution of the both compounds in a solvent can be carried out, for example, by slightly heating or under heating, and the subsequent precipitation of a less soluble diastereomeric salt can be carried out, for example, under cooling or slightly heating.

For precipitating the less soluble diastereomeric salt from the reaction mixture, it is generally not necessary to add seed crystals. However, in order to make the precipitation easier, the same kind of crystals of the desired diastereomeric salt may be added as seed crystals.

Also, after the less soluble diastereomeric salt is separated, a mother liquor is concentrated to separate and collect the other diastereomeric salt which is the more soluble diastereomeric salt, and then the salt is decomposed. Or else, the mother liquor after separating the less soluble diastereomeric salt may be extracted with a suitable organic solvent to recover the remaining optically active piperidine intermediate (IV) which is an enantiomer.

The purity of the separated and collected diastereomeric salt can be improved by recrystallization, depending on the necessity.

A salt is removed from the diastereomeric salt thus collected by the conventionally known salt decomposition method whereby the desired optically active piperidine intermediate (IV) can be obtained. For example, an optically active piperidine intermediate (IV) can be obtained by dissolving the salt in a suitable solvent (e.g., a mixed solvent of water-dimethylformamide, etc.), treating with a suitable alkali (e.g., sodium hydroxide, potassium hydroxide, etc.), extracting with a suitable extraction solvent (e.g., diethyl ether, ethyl acetate, chloroform, methylene chloride, toluene, etc.), and evaporating the extraction solvent.

Further, an aqueous layer after extraction is treated by a suitable mineral acid (e.g., hydrochloric acid, sulfuric acid, etc.) and the aqueous layer is extracted with a suitable solvent (e.g., diethyl ether, ethyl acetate, chloroform, methylene chloride, toluene, etc.), an optically active propionic acid compound (VII) or optically active N-acyl-amino acid, which is an optically resolving agent, can be recovered.

A specific example of the optically resolving process using (2R,3R)-2-hydroxy-3-(4-methoxyphenyl)-3-(2-nitro-5-chlorophenylthio)propionic acid as an optically resolving agent is described below.

3R)-2-hydroxy-3-(4-methoxyphenyl)-3-(2-nitro-5-chlorophenylthio)propionic acid, and then decomposing the said salt, (S)-4-[(4-chlorophenyl)(2-pyridyl)methoxy]-piperidine can be obtained.

In the present specification, the less soluble diastereomeric salt means a diastereomeric salt having less solubility in a solvent than the other between a pair of diastereomeric salts.

The racemic piperidine intermediate (III) of the formula (III), which is a starting material, is described in Japanese Provisional Patent Publication No. 25465/1990. The optically active propionic acid compound (VII) of the formula (VII), which is used as an optically resolving agent, can be prepared according to the method as described in, for example, Japanese Patent Publication No. 13994/1988.

Pharmacological Test

By using an (S)-ester and (R)-ester of the following optically active piperidine ester compound, difference in pharmacological effects between optical isomers were studied.

(S)-ester: ethyl (S)-4-[4-[(4-chlorophenyl)(2-pyridyl)methoxy]piperidino]butanoate fumaric acid salt (prepared in Reference example 3)

(R)-ester: ethyl (R)-4-[4-[(4-chlorophenyl) (2-pyridyl)methoxy]piperidino]butanoate fumaric acid salt (prepared in Reference example 4)

Protective Effects on Histamine-induced Death

By using Hartley male guinea pigs with a body weight of 250 to 550 g, protective effects on histamine-induced death were tested according to the method of Lands et al. (Journal

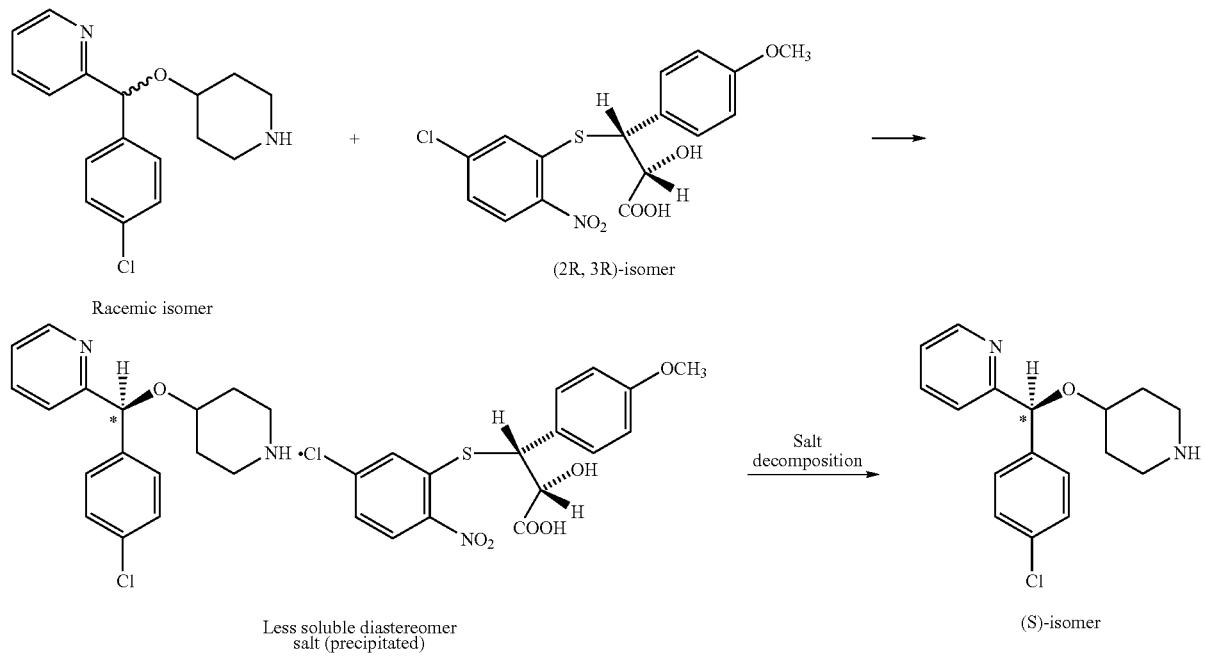

That is, by acting (2R,3R)-2-hydroxy-3-(4-methoxy-phenyl)-3-(2-nitro-5-chlorophenylthio)propionic acid (an optically resolving agent) on (±)-4-[(4-chlorophenyl)(2-pyridyl) methoxy]piperidine, separating and collecting a salt of (S)-4-[(4-chlorophenyl)(2-pyridyl)methoxy]piperidine precipitating as a less soluble diastereomeric salt and (2R, of Pharmacological Experimental Therapy, vol. 95, p. 45, 1949 (A. M. Lands, J. O. Hoppe, O. H. Siegmund, and F. F. Luduena, J. Pharmacol. Exp. Ther., 95, 45 (1949))). Test animals were fasted overnight (about 14 hours), and then 5 ml/kg of a test substance was orally administrated. Two hours after administration of the test substance, 1.25 mg/kg of histamine hydrochloride was intravenously administrated to induce histamine shock. After induction, symptom of the test animals was observed and the histamine-shock appearing time was measured, and termination of respiration or restoration was also observed. The test results are shown in Table 1.

TABLE 1

Protective effects on histamine-induced death

| Test substance | Administrated amount (mg/kg, p.o.) | n | Survival ratio (%) |
|---|---|---|---|
| (S)-ester | 0.01 | 8 | 0 |
|  | 0.02 | 7 | 42.9 |
|  | 0.03 | 8 | 62.5 |
|  | 0.06 | 8 | 100 |
|  | 0.1 | 8 | 100 |
| (R)-ester | 0.3 | 8 | 0 |
|  | 0.6 | 8 | 0 |
|  | 1.0 | 8 | 50.0 |
|  | 3.0 | 8 | 62.5 |
|  | 10.0 | 8 | 100 | n: number of used test animals

Inhibitory Effect on 7 Days Homologous PCA Reaction

By using Hartley male guinea pigs with a body weight of 250 to 550 g, inhibitory effect on PCA reaction was tested according to the method of Levine et al. (Journal of Immunology, vol. 106, p. 29, 1971 (B. B. Levine, H. Chang, Jr., and N. M. Vaz, J. Immunol. 106, 29 (1971))). 0.05 ml of guinea pig anti-BPO.BGG-IgE serum diluted 32-fold with a physiological saline was hypodermically administrated to the guinea pig through two points of right and left sandwiching the median line of the back which had been shaved one day before.

After 7 days, 1 ml of a 1% Evans Blue physiological saline solution containing 500 μg of benzylpenicilloyl bovine serum albumin (BPO.BSA) was intravenously administrated to induce a PCA reaction. Thirty minutes later, exsanguination was carried out, and the skin was peeled off and the amount of the leaked dye was measured according to the method of Katayama et al. (Microbiological Immunology, vol. 22, p. 89, 1978 (S. Katayama, H. Shinoya and S. Ohtake, Microbiol. Immunol., 22, 89 (1978))). The test animals were fasted overnight (about 16 hours) and the test substances were orally administrated 2 hours before the administration of the antigen. The test results are shown in Table 2.

TABLE 2

Inhibitory effect on 7 days homologous PCA reaction

| Test substance | Administrated amount (mg/kg, p.o.) | n | Inhibitory ratio (%) |
|---|---|---|---|
| (S)-ester | 0.01 | 10 | 37.3 |
|  | 0.02 | 8 | 46.3 |
|  | 0.03 | 9 | 56.9 |
|  | 0.06 | 8 | 63.4 |
|  | 0.1 | 8 | 58.8 |
| (R)-ester | 0.3 | 8 | −3.1 |
|  | 1.0 | 8 | 13.6 |
|  | 3.0 | 8 | 45.8 |
|  | 10.0 | 8 | 59.5 | n: number of used test animals

From the test results shown in Table 1, both of the (S)-ester and the (R)-ester showed inhibitory activities dose-dependently, and $ED_{50}$ values of the (S)-ester and the (R)-ester obtained from the dose-response curve are 0.023 mg/kg and 1.0 mg/kg, respectively, which means that the (S)-ester showed about 43-folds higher potency than the (R)-ester. Also, in the inhibitory effect on PCA reaction shown in Table 2, both of the (S)- and (R)-esters showed inhibitory activities dose-dependently. It can be estimated that the maximum inhibitory ratio of this test is expected to be about 70% or so, and when the activities are compared with a dose which inhibits 50% of the maximum value (i.e., 35%), the (S)-ester showed about 100-fold or more potency than the (R)-ester. These results show the clear difference in pharmacological effects between optical isomers and the (S)-ester is confirmed to be superior to the (R)-ester.

The above-mentioned (S)-ester is, however, hygroscopic as shown in the stability test results (Table 4) below. Though the (S)-piperidine compound of the formula (I), which is a metabolite of the (S)-ester, substantially shows the same pharmacological effects as the (S)-ester, the (S)-piperidine compound (I) itself is quite unlikely to crystallize and usually obtained as an amber syrup. Therefore, both the (S)-ester and (S)-piperidine compound (I) are difficult to secure and maintain high quality as a medicinal product.

Thus, with regard to various acid addition salts of the (S)-piperidine compounds of the formula (I), crystallization was investigated by the following methods.

Experiment 1

(S)-Piperidine compound of the formula (I) was dissolved in an organic solvent, and after adding an acid shown in Table 3 to make a uniform solution, the mixture was allowed to stand. When no precipitate is obtained, after the solvent was removed, a less polar solvent was added to the residue and the mixture was allowed to stand again. Except for the case where the acid addition salt is oily or syrupy, the obtained solid material was collected by filtration and dried under reduced pressure. Characteristics of the resulting various kinds of acid addition salts are oily product or hygroscopic crystals for the most of the cases as shown in Table 3.

TABLE 3

Characteristics of various acid addition salts of (S)-piperidine compounds (I) of the formula (I)

| Acid | Molar ratio | Solvent | Characteristics of acid addition salt |
|---|---|---|---|
| Hydrochloric acid | 1 | Diethyl ether | White crystal (hygroscopic) |
| Hydrochloric acid | 2 | Diethyl ether | White crystal (hygroscopic) |
| Hydrobromic acid | 1 | Chloroform | White crystal (hygroscopic) |
| Hydrobromic acid | 2 | Chloroform | White crystal (hygroscopic) |
| Sulfuric acid | 1/2 | Acetonitrile | White crystal (hygroscopic) |
| Sulfuric acid | 1 | Acetone | Pale yellowish crystal (hygroscopic) |
| Methanesulfonic acid | 1 | Acetone | Pale yellowish oily product |
| Methanesulfonic acid | 2 | Methylene chloride | Pale yellowish oily product |
| Fumaric acid | 1/2 | Ethanol | Amber syrupy product |
| Fumaric acid | 1 | Ethyl acetate | Crystal containing much amount of fumaric acid |
| Fumaric acid | 2 | Ethanol[a] | Crystal containing much amount of fumaric acid |

TABLE 3-continued

Characteristics of various acid addition salts of
(S)-piperidine compounds (I) of the formula (I)

| Acid | Molar ratio | Solvent | Characteristics of acid addition salt |
|---|---|---|---|
| Maleic acid | 1/2 | Ethanol | Amber syrupy product |
| Maleic acid | 1 | Ethyl acetate | Amber syrupy product |
| DL-Mandelic acid | 1 | Ethanol[b] | Amber syrupy product |
| Succinic acid | 1 | Ethanol[b] | Oily product |
| L(+)-Tartaric acid | 1 | Ethanol[b] | Foamy product (hygroscopic) |
| Hibenzic acid | 1 | Acetone | Amber syrupy product |
| Fendizoic acid | 1 | Ethanol[b] | Amber syrupy product |
| L-Lactic acid | 1 | Acetonitrile | Oily product |
| DL-Malic acid | 1 | Ethanol[b] | Amber syrupy product |
| 4-Acetamidobenzoic acid | 1 | Ethanol[b] | Amber syrupy product |

[a] After removal of ethanol, acetonitrile was added and the mixture was allowed to stand.
[b] After removal of ethanol, ethyl acetate was added and the mixture was allowed to stand.

However, benzenesulfonic acid salt and benzoic acid salt of the (S)-piperidine compound of the formula (I) were obtained as non-hygroscopic crystals.

Stability Test

Benzenesulfonic acid salt: (S)-4-[4-[(4-chlorophenyl)(2-pyridyl)methoxy]piperidino]butanoic acid monobenzenesulfonic acid salt (prepared in Example 2)

Benzoic acid salt: (S)-4-[4-[(4-chlorophenyl)(2-pyridyl)methoxy]piperidino]butanoic acid monobenzoic acid salt (prepared in Example 3)

After pulverizing the above-mentioned respective compounds, powder passed through a 500 μm sieve was made to be a test sample. Respective samples were divided and placed in glass Petri dishes and preserved at 40° C. and 75% relative humidity. One month later, the samples were taken out, and a weight of contained analogues and a content of (R)-isomer by racemization were measured and compared with those at the beginning of the test.

(a) Change in content of analogous substances

The sample was dissolved in a mobile phase and the solution was adjusted so as to contain about 0.1% of the sample per ml. With regard to 25 μl of the sample solution, percentages of the respective peak area were measured by a liquid chromatography using an automatic integration method.

Operation Conditions

Detector: UV light absorption photometer (225 nm)
Column: Cosmosil 5 ph 4.6 mm×150 mm (trade name, available from Nakarai Tesc Co.)
Column temperature: room temperature
Mobile phase:
(S)-ester: A mixed solution of 0.01 M potassium dihydrogen phosphate buffer (adjusted to pH 5.8 with 0.1 N aqueous sodium hydroxide solution) and acetonitrile (65:35)
Benzenesulfonic acid salt, Benzoic acid salt: A mixed solution of 0.01 M potassium dihydrogen phosphate buffer (adjusted to pH 5.8 with 0.1 N aqueous sodium hydroxide solution) and acetonitrile (72:28)

Flow rate: 0.9 ml/min
Range of peak measurement: Range within 50 minutes after injection of samples (b) Amount of (R)-isomer About 5 mg of the sample was dissolved in the mobile phase and the solution was adjusted so as to contain about 0.1% of the sample per ml. With regard to 1.5 μl of the sample solution, percentages of the respective peak area were measured by a liquid chromatography using an automatic integration method, and an amount of the (R)-isomer (%) was calculated by the following equation.

$$\text{Amount of } (R)\text{-isomer } (\%) = \frac{Q^R}{Q^S + Q^R} \times 100$$

$Q^S$: percentage of peak area of (S)-isomer
$Q^R$: percentage of peak area of (R)-isomer Operation Conditions Detector: UV light absorption photometer (220 nm)
Column: ULTRON ES-OVM 4.6 mm×150 mm (trade name, available from Shinwa Kako Co.)
Column temperature: room temperature
Mobile phase:
(S)-ester: A mixed solution of 0.02 M potassium dihydrogen phosphate buffer (adjusted to pH 4.6 with 0.1 N aqueous sodium hydroxide solution) and ethanol (100:13)
Benzenesulfonic acid salt, Benzoic acid salt: A mixed solution of 0.02 M potassium dihydrogen phosphate buffer (adjusted to pH 5.5 with 0.1 N aqueous sodium hydroxide solution) and acetonitrile (100:16)
Flow rate: 0.9 ml/min
Range of peak measurement: Range about twice of the retention time of the (S)-isomer
Retention time: (R)-isomer about 7 to 10 minutes
(S)-isomer about 13 to 15 minutes

TABLE 4

| | (S)-ester of Reference example 3 | | Benzenesulfonic acid salt | | Benzoic acid salt | |
|---|---|---|---|---|---|---|
| | Beginning | 1 month later | Beginning | 1 month later | Beginning | 1 month later |
| Content of analogue substance | % 1.72 | % 2.65 | % 0.15 | % 0.16 | % 1.20 | % 1.20 |
| Content of (R)-isomer | 0.87 | 1.15 | 0.37 | 0.39 | 0.37 | 0.40 |
| Appearance | White powder | Slightly colored | White powder | Unchanged | White powder | Unchanged |
| Amount of moisture absorption | | 0.45 | | 0.18 | | 0.05 |

From the test results shown in Table 4, it was clarified that increase in analogous substances due to decomposition can be markedly admitted in the (S)-ester and optical purity is decreased accompanying with increase in the (R)-isomer. Accordingly, (S)-ester is physicochemically unstable and it cannot be concluded that the compound can secure and maintain high quality as a medicine for a long period of term. On the other hand, it can be confirmed that in the benzenesulfonic acid salt and benzoic acid salt, remarkable increases in analogous substances and the content of (R)-isomer are not observed and the amount of moisture absorption is only a little. Accordingly, these salts are the compounds having excellent physicochemical stabilities as optically active isomers.

As described above, a benzenesulfonic acid salt and a benzoic acid salt of the (S)-piperidine compounds (I) are superior optical isomers having higher antihistaminic activity and antiallergic activity, and act as an active component in vivo. Also, they show excellent physicochemical stabilities so that they have properties suitable for a medicinal product.

EXAMPLES

The present invention will be explained in more detail by referring to Reference examples and Examples, but the scope of the present invention is not limited by these.

Reference Example 1

(S)-(−)-4-[(4-chlorophenyl)(2-pyridyl)methoxy]-piperidine (1) In 1000 ml of methyl acetate was dissolved 18.58 g (61.36 mmol) of (±)-4-[(4-chlorophenyl)(2-pyridyl)-methoxy]piperidine under heating, and 6.93 g (18.42 mmol) of (−)-dibenzoyl-L-tartaric acid monohydrate was added to the mixture and the resulting mixture was stirred. White crystals precipitated (Crystal 1) were collected by filtration and the filtrate was concentrated under reduced pressure. The filtrate was concentrated to 100 ml and white crystals (Crystal 2) further precipitated were collected by filtration, and the filtrate was again concentrated under reduced pressure. The resulting crystals and the concentrate of the filtrate were analyzed for their compositional ratio ((S) isomer:(R) isomer) of the respective optical isomers by high performance liquid chromatography with a chiral column.

Crystal 1: 18.37 g ((S) isomer:(R) isomer=29.51:70.49)

Crystal 2: 0.57 g ((S) isomer:(R) isomer=33.42:66.58)

Concentrate of filtrate: 7.70 g ((S) isomer:(R) isomer=79.94:20.06)

(2) In 280 ml of ethanol was dissolved 7.70 g (25.43 mmol) of the concentrate of the filtrate obtained in the above-mentioned (1) under heating, and 3.82 g (25.45 mmol) of L-(+)-tartaric acid was added and the mixture was again heated to prepare a uniform solution. After gradually cooling, a small amount of seed crystals was added to the mixture and the mixture was allowed to stand. Precipitated crystals were collected by filtration and dried at 40° C. under reduced pressure. Yield: 8.68 g ((S) isomer:(R) isomer=87.44:12.56).

(3) As for 8.68 g of the white crystals obtained in the above-mentioned (2), recrystallization from ethanol was repeated until the purity of (S) isomer exceeds 99.5% (optical purity: 99.0% d.e.).

Yield: 3.87 g ((S) isomer:(R) isomer=99.72:0.28).

(4) To 2.13 g (4.70 mmol) of the white crystals obtained in the above-mentioned (3) was added 15 ml of a 1N aqueous sodium hydroxide solution and the mixture was extracted with about 50 ml of chloroform. The extract was washed with water, dried over anhydrous sodium sulfate, and concentrated to afford the objected (S)-(−)-4-[(4-chlorophenyl)(2-pyridyl)methoxy]piperidine as a pale yellowish oily product.

Yield: 1.40 g (yield: 98.6%).

$[\alpha]_D^{24}$ −10.0° (c=1, MeOH)

Reference Example 2

(R)-(+)-4-[(4-chlorophenyl)(2-pyridyl)methoxy]-piperidine (1) To the crystal 1 obtained in Reference example 1(1) was added 200 ml of 0.5N aqueous sodium hydroxide solution and the mixture was extracted with about 100 ml of toluene twice. The extract was washed with a saturated saline solution, dried over anhydrous sodium sulfate and concentrated to afford 10.29 g of pale yellowish oily product.

(2) In 500 ml of methyl acetate was dissolved 10.29 g of the pale yellowish oily product obtained in the above-mentioned (1) under heating, and 1.96 g (5.21 mmol) of (+)-dibenzoyl-D-tartaric acid monohydrate was added and the mixture was stirred. Precipitated white crystals were collected by filtration and the filtrate was concentrated under reduced pressure. The resulting crystals and the concentrate of the filtrate were analyzed for their compositional ratio ((S) isomer:(R) isomer) of the respective optical isomers by using high performance liquid chromatography with a chiral column.

White crystal: 4.31 g ((S) isomer:(R) isomer=65.52:34.48)
Concentrate of filtrate: 7.93 g ((S) isomer:(R) isomer=16.61:83.39)

(3) In 400 ml of ethanol were dissolved 7.90 g (26.09 mmol) of the concentrate of the filtrate obtained in the above-mentioned (2) and 3.90 g (25.98 mmol) of D-(−)-tartaric acid under heating, and the mixture was allowed to stand at room temperature over night. Precipitated crystals were collected by filtration and dried under reduced pressure at 40° C. Yield: 8.56 g ((S) isomer:(R) isomer=9.05:90.95)

(4) As for 8.55 g of the white crystals obtained in the above-mentioned (3), recrystallization from ethanol was repeated until the purity of (R) isomer exceeds 99.5% (optical purity: 99.0% d.e.).

Yield: 4.15 g ((S) isomer:(R) isomer=0.24:99.76).

(5) To 4.00 g (8.83 mmol) of the white crystals obtained in the above-mentioned (4) was added 15 ml of a 1N aqueous sodium hydroxide solution and the mixture was extracted with about 50 ml of chloroform. The extract was washed with water, dried over anhydrous sodium sulfate and concentrated to afford the objected (R)-(+)-4-[(4-chlorophenyl)(2-pyridyl)-methoxy]piperidine as a pale yellowish oily product. Yield: 2.66 g (yield: 99.6%).

$[\alpha]_D^{23.5}$ +12.2° (c=2, MeOH)

Reference Example 3

Synthesis of ethyl (S)-4-[4-[(4-chlorophenyl)(2-pyridyl)methoxy]piperidino]butanoate fumaric acid salt (1) In 15 ml of acetone was dissolved 1.33 g (4.39 mmol, optical purity: 99.4% e.e.) of (S)-(−)-4-[(4-chlorophenyl)(2-pyridyl)methoxy]piperidine obtained according to Reference example 1, then, 1.03 g (5.28 mmol) of ethyl 4-bromobutanoate and 0.73 g (5.28 mmol) of potassium carbonate were added, and the mixture was refluxed under stirring for 7 hours. Insolubles were filtered off and the filtrate was concentrated under reduced pressure. The resulting slightly yellowish oily product was purified by silica gel column chromatography using a mixed solvent of chloroform and methanol (volume ratio: 30:1) as an eluent. Fractions containing the isolated objective compound were concentrated under reduced pressure to afford 1.71 g of ethyl (S)-4-[4-[(4-chlorophenyl)(2-pyridyl)methoxy]piperidino]-butanoate as an oily product (Yield: 93.4%, optical purity: 99.4% e.e.).

$[\alpha]_D^{25}$ −6.6° (c=1, MeOH)

(2) In 40 ml of ethanol were dissolved 1.70 g (4.08 mmol) of the ethyl ester obtained in the above-mentioned (1) and 0.48 g (4.14 mmol) of fumaric acid to form a uniform solution, and the mixed solution was concentrated under reduced pressure. To the residue was added 18 ml of ethyl acetate to form a uniform solution again, and the solution was allowed to stand overnight by adding a small amount of seed crystals. Precipitated crystals were collected by filtration to afford 1.97 g (Yield: 90.1%, optical purity: 99.0% e.e.) of the objected ethyl (S)-4-[4-[(4-chlorophenyl)(2-pyridyl)-methoxy]piperidino]butanoate fumaric acid salt. Melting point 123 to 124° C.

Elemental analysis value (%): as $C_{22}H_{29}ClN_2O_3 \cdot C_4H_4O_4$
Calculated: C, 60.84; H, 6.24; N, 5.26
Found: C, 60.73; H, 6.32; N, 5.21

Reference Example 4

Synthesis of ethyl (R)-4-[4-[(4-chlorophenyl)(2-pyridyl)methoxy]piperidino]butanoate fumaric acid salt (1) By using (R)-(+)-4-[(4-chlorophenyl)(2-pyridyl)-methoxy]piperidine (optical purity: 99.5% e.e.) obtained according to Reference example 2, ethyl (R)-4-[4-[(4-chlorophenyl)(2-pyridyl)methoxy]piperidino]butanoate (optical purity: 99.5% e.e.) was obtained in the same manner as in Reference example 3(1). $[\alpha]_D^{25}$ +6.6° (c=1, MeOH)

(2) By using the ethyl ester obtained in the above-mentioned (1), ethyl (R)-4-[4-[(4-chlorophenyl)(2-pyridyl)methoxy]piperidino]butanoate fumaric acid salt (optical purity: 99.3% e.e.) was obtained in the same manner as in Reference example 3(2). Melting point: 117 to 119° C.

Elemental analysis value (%): as $C_{22}H_{29}ClN_2O_3 \cdot C_4H_4O_4$
Calculated: C, 60.84; H, 6.24; N, 5.26
Found: C, 60.65; H, 6.11; N, 5.06

Example 1

Synthesis of (S)-4-[4-[(4-chlorophenyl)(2-pyridyl)-methoxy]piperidino]butanoic acid.

In 760 ml of ethanol was dissolved 126.0 g (0.302 mol) of ethyl (S)-4-[4-[(4-chlorophenyl)(2-pyridyl)methoxy]-piperidino]butanoate obtained according to Reference example 3(1), and then 120.8 ml of a 5N aqueous sodium hydroxide solution was added to the mixture and the mixture was allowed to stand at room temperature overnight. After confirming disappearance of the starting materials, the mixture was neutralized by adding 121.1 ml of a 5N hydrochloric acid. After the precipitated crystals were removed by filtration, the reaction mixture was concentrated under reduced pressure. To the residue was added 600 ml of methyl acetate, and the solution was again concentrated under reduced pressure. The residue was dissolved in 600 ml of dichloromethane and dried over anhydrous magnesium sulfate sufficiently. Insolubles were removed by filtration, the filtrate was concentrated to afford the desired compound as an orange syrupy product (125.3 g). When the syrupy product was further dried under reduced pressure, it became a foamy product (120.2 g).

$[\alpha]_D^{25}$ +3.4° (c=5, MeOH)

Example 2

Synthesis of (S)-4-[4-[(4-chlorophenyl)(2-pyridyl)-methoxy]piperidino]butanoic acid monobenzene-sulfonic acid salt In 25 ml of ethyl acetate was dissolved 0.5 g (1.29 mmol) of (S)-4-[4-[(4-chlorophenyl)(2-pyridyl)methoxy]piperidino]butanoic acid obtained according to Example 1, and then, 0.20 g (1.14 mmol) of benzenesulfonic acid monohydrate was added and the mixture was concentrated under reduced pressure. To the residue was added again 25 ml of ethyl acetate and the mixture was allowed to stand for about one week, part of the syrupy product was crystallized. When the material was stirred by a spatula and further allowed to stand, whole parts were crystallized. This crystals were recrystallized from 5 ml of acetonitrile to afford 0.42 g (Yield: 67.3%, optical purity: 99.2% e.e.) of the desired product as pale gray prisms.

$[\alpha]_D^{20}$ +6.0° (c=5, MeOH). Melting point: 161 to 163° C.
Elemental analysis value (%): as $C_{21}H_{26}ClN_2O_3 \cdot C_6H_7O_3S$
Calculated: C, 59.28; H, 5.71; N, 5.12
Found: C, 59.27; H, 5.74; N, 5.10

Example 3

Synthesis of (S)-4-[4-[(4-chlorophenyl)(2-pyridyl)-methoxy]piperidino]butanoic acid monobenzoic acid salt In 30 ml of acetone was dissolved 0.91 g (2.34 mmol) of (S)-4-[4-[(4-chlorophenyl)(2-pyridyl)methoxy]piperidino]-butanoic acid obtained according to Example 1, and then, 0.29 g (2.37 mmol) of benzoic acid was added to the solution and the mixture was made uniform. Then, the mixture was concentrated under reduced pressure. To the residue was added 50 ml of isopropyl ether and the mixture was allowed to stand for two days, part of the syrupy product was crystallized. When the material was stirred by a spatula and further allowed to stand, whole parts were crystallized. This crystals were recrystallized from 36 ml of ethyl acetate to afford 0.87 g (Yield: 72.8%, optical purity: 99.4% e.e.) of the desired product as white powder crystals.

$[\alpha]_D^{23}$ −4.6° (c=1, EtOH). Melting point: 136 to 140° C.

In the following examples, a quantitative ratio (enantiomer excessive rate: % e.e.) of (R)- and (S)-piperidine intermediates was analyzed according to the following conditions by a high performance liquid chromatography (HPLC).

Column: ULTORON-ES-OVM (4.6 φ×150 mm) (available from Shinwa Kako K. K.)

Mobile phase: 20 mM $KH_2PO_4$ aqueous solution (pH 4.6)/ethanol (Examples 4 to 7; 100:10, Examples 8 to 20; 100:6)

Flow rate: 1.0 ml/min

Detection wavelength: UV-220 nm

Example 4

(1) In a mixed solution of 30 ml of ethanol and 7 ml of water were dissolved under heating 1.00 g of (±)-4-[(4-chlorophenyl)(2-pyridyl)methoxy]piperidine and 1.27 g of (2R,3R)-2-hydroxy-3-(4-methoxyphenyl)-3-(2-nitro-5-chlorophenylthio)propionic acid, and after gradually cooling, the mixture was stirred at 25° C. for 2 hours. Precipitated crystals were collected by filtration, washed with ethanol, and dried at 50° C. under reduced pressure to afford 0.97 g of crude crystals of a salt of (S)-4-[(4-chlorophenyl) (2-pyridyl)methoxy]piperidine and (2R,3R)-2-hydroxy-3-(4-methoxyphenyl)-3-(2-nitro-5-chlorophenyl-thio)propionic acid.

$[\alpha]_D^{25}$ −11.7° (c=1, dimethylformamide)
94.1% d.e.

(2) 0.80 g of this crude crystals was recrystallized from a mixed solution of 20 ml of ethanol and 4 ml of water to afford 0.71 g of crystals.

$[\alpha]_D^{25}$ −10.9° (c=1, dimethylformamide)
100% d.e.

(3) 0.35 g of this recrystallized material was dissolved in a mixed solution of 3 ml of water and 0.5 ml of dimethylformamide, then decomposed by adding 0.76 ml of a 1M aqueous sodium hydroxide solution and extracted three times with diethyl ether. The diethyl ether layer was washed with a saturated saline solution, dried over anhydrous sodium sulfate, and diethyl ether was distilled off to afford 0.14 g of the desired (S)-4-[(4-chlorophenyl)(2-pyridyl) methoxy]piperidine as an oily product.

$[\alpha]_D^{25}$ −21.6° (c=0.99, ethanol)
100% e.e.

Example 5

By treating (±)-4-[(4-chlorophenyl)(2-pyridyl)-methoxy] piperidine and (2R,3R)-2-hydroxy-3-(4-methoxy-phenyl)-3-(2-nitrophenylthio)propionic acid in the same manner as in Example 4-(1), (2) and (3) to afford (S)-4-[(4-chlorophenyl)(2-pyridyl)methoxy]piperidine.

Example 6

(1) In a mixed solution of 25 ml of ethanol and 5 ml of water were dissolved under heating 2.00 g of (±)-4-[(4-chlorophenyl)(2-pyridyl)methoxy]piperidine and 1.52 g of (2R,3R)-2-hydroxy-3-(4-methoxyphenyl)-3-(2-nitro-5-chlorophenylthio)propionic acid, and after adding a small amount of seed crystals at 50° C., the mixture was stirred at 25° C. for 2 hours. Precipitated crystals were collected by filtration, washed with ethanol, and dried at 50° C. under reduced pressure to afford 1.95 g of crude crystals of a salt of (S)-4-[(4-chlorophenyl)(2-pyridyl)methoxy]piperidine and (2R,3R)-2-hydroxy-3-(4-methoxyphenyl)-3-(2-nitro-5-chlorophenylthio)propionic acid.

$[\alpha]_D^{26}$ −11.6° (c=1, dimethylformamide)
94.0% d.e.

(2) 1.70 g of this crude crystals were recrystallized from a mixed solution of 42 ml of ethanol and 8.5 ml of water to afford 1.53 g of crystals.

$[\alpha]_D^{25}$ −11.0° (c=1, dimethylformamide)
100% d.e.

(3) This recrystallized product was treated in the same manner as in Example 4-(3) to afford (S)-4-[(4-chlorophenyl)(2-pyridyl)methoxy]piperidine.

Example 7

(1) In a mixed solution of 10 ml of ethanol and 2 ml of water were dissolved under heating 1.00 g of (±)-4-[(4-chlorophenyl)(2-pyridyl)methoxy]piperidine and 1.15 g of (2S,3S)-2-hydroxy-3-(4-methoxyphenyl)-3-(2-nitrophenylthio)propionic acid, and after gradually cooling, the mixture was stirred at 25° C. for 2 hours. Precipitated crystals were collected by filtration, washed with ethanol, and dried at 50° C. under reduced pressure to afford 0.84 g of crude crystals of a salt of (R)-4-[(4-chlorophenyl)(2-pyridyl)methoxy]-piperidine and (2S,3S)-2-hydroxy-3-(4-methoxyphenyl)-3-(2-nitrophenylthio)propionic acid.

$[\alpha]_D^{25}$ −40.6° (c=1, dimethylformamide)
89.8% d.e.

(2) 0.70 g of this crude crystals was recrystallized from a mixed solution of 8.4 ml of ethanol and 0.9 ml of water to afford 0.61 g of crystals.

$[\alpha]_D^{25}$ −38.9° (c=1, dimethylformamide)
100% d.e.

(3) 0.50 g of this recrystallized product was treated in the same manner as in Example 4-(3) to afford 0.21 g of (R)-4-[(4-chlorophenyl)(2-pyridyl)methoxy]piperidine.

$[\alpha]_D^{25}$ +21.3° (c=1, ethanol)
100% e.e.

Example 8

(1) In 400 ml of ethyl acetate were dissolved 10 g (33 mmol) of (±)-4-[(4-chlorophenyl)(2-pyridyl)methoxy]-piperidine and 4.1 g (19.8 mmol) of N-acetyl-L-phenylalanine under heating at 50 to 60° C., and after cooling to about 40° C., a small amount of seed crystals of (S)-4-[(4-chlorophenyl)(2-pyridyl)methoxy]piperidine.N-acetyl-L-phenyl-alanine was added to the mixture. After gradually cooling, the mixture was stirred at about 30° C. for one hour, and further stirred at 25° C. for 3 hours. Precipitated crystals were collected by filtration, washed with 40 ml of ethyl acetate, and dried at 50 to 60° C. to afford 7.14 g (yield: 42.4%) of crude crystals of a salt of (S)-4-[(4-chlorophenyl)(2-pyridyl) methoxy]piperidine.N-acetyl-L-phenylalanine.

$[\alpha]_D^{23}$ +30.2° (c=1, methanol)
95.2% d.e.

(2) In 350 ml of ethyl acetate was dissolved 7.0 g of this crude crystals under reflux, and after gradually cooling, the mixture was stirred at about 30° C. for one hour and then at 20° C. for 3 hours. Precipitated crystals were collected by filtration and washed with 40 ml of ethyl acetate, and dried at 50 to 60° C. to afford 6.44 g of crystals (recrystallization yield: 92.0%).

$[\alpha]_D^{23}$ +29.6° (c=1, methanol)
98.9% d.e.

(3) In 30 ml of water was dissolved 6.0 g (11.7 mmol) of this recrystallized product, then 12.9 ml of 2M hydrochloric acid was added and the mixture was extracted with 20 ml of ethyl acetate three times to recover N-acetyl-L-phenylalanine. To the aqueous layer was added 10.3 ml of a 5M aqueous sodium hydroxide solution, and the mixture was extracted three times with 20 ml of ethyl acetate, and the extract was washed with a saturated saline solution and dried over anhydrous magnesium sulfate. The solvent was removed to afford 3.45 g (yield: 96.9%) of the desired (S)-4-[(4-chlorophenyl)(2-pyridyl)methoxy]piperidine as oily product.

$[\alpha]_D^{25}$ −21.4° (c=1, ethanol)
99.0% e.e.

The amount of the recovered N-acetyl-L-phenylalanine was 2.15 g (yield: 88.2%) and $[\alpha]_D^{25}$ was +40.3° (c=1, methanol).

(4) The mother liquor subjected to optical resolution obtained in the above (1) was concentrated. To the residue was added 20.9 ml of 2M hydrochloric acid, and the mixture was extracted with 20 ml of ethyl acetate three times to recover N-acetyl-L-phenylalanine. To the aqueous layer was added 16.7 ml of a 5M aqueous sodium hydroxide solution, and the mixture was extracted with 20 ml of ethyl acetate three times. The extract was washed with a saturated saline solution and then dried over anhydrous magnesium sulfate. The solvent was removed to afford 6 g of 4-[(4-chlorophenyl)(2-pyridyl)methoxy]piperidine having an optical purity of 63.9% e.e. in which an (R)-isomer is excessive. Also, 1.02 g of recovered N-acetyl-L-phenylalanine was obtained and $[\alpha]_D^{25}$ thereof was +40.3° (c=1, methanol).

Examples 9 to 20

According to the method of Example 8-(1), (±)-4-[(4-chlorophenyl)(2-pyridyl)methoxy]piperidine was optically resolved by using an optically resolving agent and a solvent shown in Table 5. As for the respective diastereomeric salts obtained, analysis with the above-mentioned HPLC conditions was carried out and the results are also shown in Table 5.

TABLE 5

| | Optically resolving agent[a] (optically active N-acyl-amino acid) | Solvent | Diastereomeric salt[b] Yield (%) | Chiral HPLC[c] (R):(S) |
|---|---|---|---|---|
| 9 | N-acetyl-L-phenylalanine | Acetonitrile | 29.7 | 4:96 |
| 10 | N-acetyl-L-phenylalanine | Ethyl acetate | 41.8 | 6:94 |
| 11 | N-acetyl-L-leucine | Ethyl acetate | 58.1 | 37:63 |
| 12 | N-acetyl-L-leucine | Ethyl acetate/2-propanol[d] | 18.1 | 3:97 |
| 13 | N-acetyl-L-leucine | Acetonitrile | 44.6 | 29:71 |
| 14 | N-tosyl-L-glutamic acid | Methanol/water[e] | 47.4 | 80:20 |
| 15 | N-benzyloxycarbonyl-L-phenylalanine | 2-Propanol | 57.0 | 35:65 |
| 16 | N-benzyloxycarbonyl-L-methionine | Acetonitrile | 36.2 | 88:12 |
| 17 | N-benzyloxycarbonyl-D-phenylglycine | 2-Propanol | 13.0 | 61:39 |
| 18 | N-benzyloxycarbonyl-L-valine | Acetonitrile | 30.1 | 21:79 |
| 19 | N-benzyloxycarbonyl-L-threonine | Ethyl acetate/2-propanol[f] | 17.7 | 21:79 |
| 20 | N-benzyloxycarbonyl-L-serine | 2-Propanol | 57.0 | 35:65 |

[a] One molar ratio was used based on (±)-4-[(4-chlorophenyl)(2-pyridyl)methoxy]piperidine.
[b] Yield based on (±)-4-[(4-chlorophenyl)(2-pyridyl)-methoxy]piperidine. Optically active N-acyl-amino acid.
[c] Quantitative ratio of (R)- and (S)-4-[(4-chlorophenyl)(2-pyridyl)methoxy]piperidine.
[d] Ethyl acetate:2-propanol = 14:1 (volume ratio)
[e] Methanol:water = 2:1 (volume ratio)
[f] Ethyl acetate:2-propanol = 3:1 (volume ratio)

Example 21

By using respective optically active piperidine intermediates obtained in the above-mentioned Examples 4-20, respective butanoic acids were prepared according to Reference example 3 and Example 1. The resulting respective butanoic acids were treated in the same manner as in Example 2 or Example 3 to give a butanoic acid-benzenesulfonic acid salt or a butanoic acid-benzoic acid salt, respectively. The resulting butanoic acid-benzenesulfonic acid salt or butanoic acid-benzoic acid salt had the same properties as those obtained in Example 2 or Example 3, respectively.

In the description of Examples of the present specification, "d.e." of the diastereomeric salt means an "e.e." of 4-[(4-chlorophenyl)(2-pyridyl)methoxy]piperidine contained in a salt.

The invention claimed is:

1. (S)-(−)-4-[(4-chlorophenyl)(2-pyridyl)methoxy]piperidine represented by the formula (IV):

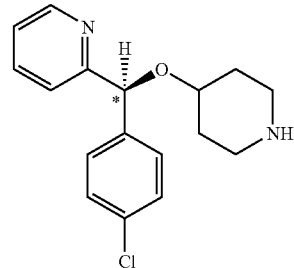

(IV)

wherein * represents an asymmetric carbon.